(12) United States Patent
Kumar et al.

(10) Patent No.: US 6,274,788 B1
(45) Date of Patent: Aug. 14, 2001

(54) BICISTRONIC DNA CONSTRUCT COMPRISING X-MYC TRANSGENE FOR USE IN PRODUCTION OF TRANSGENIC ANIMAL MODEL SYSTEMS FOR HUMAN HEPATOCELLULAR CARCINOMA AND TRANSGENIC ANIMAL MODEL SYSTEMS SO PRODUCED

(75) Inventors: Vjay Kumar; Mahavir Singh; Satish Totey; Rajesh Anand, all of New Delhi (IN)

(73) Assignees: International Centre for Genetic Engineering and Biotechnology; National Institute of Immunology, both of New Delhi (IN)

( * ) Notice: Subject to any disclaimer, the term of this patent is extended or adjusted under 35 U.S.C. 154(b) by 0 days.

(21) Appl. No.: 09/243,282

(22) Filed: Feb. 2, 1999

(30) Foreign Application Priority Data

Sep. 23, 1998 (IN) .......................................... 2858/98

(51) Int. Cl.⁷ .......................... A01K 67/07; G01N 33/00; C07H 21/04
(52) U.S. Cl. ..................................... 800/18; 800/3; 800/8; 536/23.5; 536/24.33
(58) Field of Search ............................. 435/320.5, 320.1, 435/91.2; 536/24.33, 235; 800/8, 3

(56) References Cited

U.S. PATENT DOCUMENTS 5,891,718 * 4/1999 Hobart et al. ........................ 435/325
5,925,803 * 7/1999 Leder et al. .............................. 800/3

OTHER PUBLICATIONS

Mullins JJ et al. Hypertension 22:630–633,1993.*
Cameron ER. Molecular Biotechnology 7:253–265, 1997.*
Hammer RE et al. Cell 63:1099–1112.1990.*
Seidel GE. J. Anim. Sci. 71(Suppl. 3):26–33, 1993.*
Hsu T et al. Cell 55:627–635, 1988.*
Terradillos, O., et al. "The hepatitis B virus X gene potentiates c–myc–induced liver oncogenesis in transgenic mice." *Oncogene*, vol. 14 (1997) pp. 395–404.
Kim, C., et al. "HBx gene of hepatitis B virus induces liver cancer in transgenic mice." *Nature*, vol. 351 (May 23, 1991) pp. 317–320.
Lee, T., et al. "Hepatitis B Virus Transactivator X Protein Is Not Tumorigenic in Transgenic Mice." *Journal of Virology*, vol. 64, No. 12 (Dec. 1990) pp. 5939–5947.
Koike, K., et al. "High–level Expression of Hepatitis B Virus HBx Gene and Hepatocarcinogenesis in Transgenic Mice." *Hepatology*, vol. 19, No. 4 (1994) pp. 810–819.

(List continued on next page.)

*Primary Examiner*—Karen M. Hauda
*Assistant Examiner*—Ram R. Shukla
(74) *Attorney, Agent, or Firm*—Ladas & Parry

(57) ABSTRACT

The present invention relates to a bicistronic DNA construct comprising X-myc transgene. In particular, the present invention relates to a bicistronic X15-myc transgene capable of expressing truncated X protein and a full-length murine c-myc protein. More particularly, the present invention relates to a bicistronic DNA construct being an X15-myc transgene for use in the production of transgenic animal model systems for human hepatocellular carcinoma and transgenic animal model systems so produced. The invention is based partially on the discovery that in susceptible transgenic mice that carry a bicistronic X-myc transgene there is an accelerated formation of liver tumors involving all lobes.

5 Claims, 8 Drawing Sheets

(4 of 8 Drawing Sheet(s) Filed in Color)

OTHER PUBLICATIONS

Perfumo, S., et al. "Recognition Efficiency of the Hepatitis B Virus Polyadenylation Signals Is Tissue Specific in Transgenic Mice." *Journal of Virology*, vol. 66, No. 11, (Nov. 1992) pp. 6819–6823.

Homburger, F., et al. "Aging Changes in CD® –1 HaM–ICR Mice Reared Under Standard Laboratory Conditions." *Journal of the National Cancer Institute*, vol. 55, No. 1 (Jul. 1975) pp. 37–43.

Schaefer, S., et al. "In vitro Transformation by Hepatitis B Virus DNA" *Intervirology*, vol. 38 (1995) pp. 143–154.

Wang, X., et al. "Abrogation of p53–induced Apoptosis by the Hepatitis B Virus X Gene." *Cancer Research* (Dec. 15, 1995) pp. 6012–6016.

Klein, N., et al. "Activation of Src Family Kinases by Hepatitis B Virus HBx Protein and Coupled Signaling to Ras." *Molecular and Cellular Biology*, vol. 17, No. 11 (Nov. 1997) pp. 6427–6436.

Chirillo, P., et al. "Hepatitis B Virus pX Activates $NF-_{\kappa}$-B–Dependent Transcription through a Raf–Independent Pathway" *Journal of Virology*, vol. 70, No. 1 (Jan. 1996) pp. 641–646.

Kekule, A., et al. "Hepatitis B virus transactivator HBx uses a tumour promoter signalling pathway" *Nature*, vol. 361 (Feb. 25, 1993) pp. 742–745.

Paterlini, P., et al. "Selective Accumulation of the X Transcript of Hepatitis B Virus in Patients Negative for Hepatitis B Surface Antigen With Hepatocellular Carcinoma" *Hepatology*, vol. 21, No. 2. (Feb. 1995) pp. 313–321.

Quignon, F., et al. "A functional N–myc2 retroposon in ground squirrels: implications for hepadnavirus–associated carcinogenesis" *Oncogene*, vol. 12 (1996) pp. 2011–2017.

Hatada, I., et al. "Co–amplification of integrated hepatitis B virus DNA and tranfsorming gene hst–1 in a hepatocellular carcinoma." *Oncogene*, vol. 3 (1988) pp. 537–540.

Dejean, A., et al. "Hepatitis B virus DNA integration in a sequence homologous to v–erb–A and steroid receptor genes in a hepatocellular carcinoma" *Nature*, vol. 322 (Jul. 3, 1986) pp. 70–72.

Wang, J., et al. "Hepatitis B virus integration in a cyclin A gene in hepatocellular carcinoma." *Nature*, vol. 343 (Feb. 8, 1990) pp. 555–557.

Fourel, G., et al. "Frequent activation of N–myc genes by hepadnavirus insertion in woodchuck liver tumours." *Nature*, vol. 347 (Sep. 20, 1990) pp. 294–298.

Wagner, E.F., et al. "The human β–globin gene and a functional viral thymidine kinase gene in developing mice." *Proc. Natl. Acad. Sci. USA*, vol. 78, No. 8 (Aug. 1981) pp. 5016–5020.

Moroy, T., et al. "Rearrangement and enhanced expression of c–myc in hepatocellular carcinoma of hepatitis virus infected woodchucks." *Nature*, vol. 324 (Nov. 20, 1986) pp. 276–279.

Peng, S., et al. "Amplification of the c–myc Gene in Human Hepatocellular Carcinoma: Biologic Significance" *J. Formos. Med. Assoc.*, vol. 92, No. 10 (1993) pp. 866–870.

Kumar, V., et al. "A truncated mutant (residues 58–140) of the hepatitis B virus X protein retains transactivation function" *Proc. Natl. Acad. Sci. USA*, vol. 93 (May 1996) pp. 5647–5652.

\* cited by examiner

FIGURE 3A

```
DraI       10         20         30         40         50
TTTAAACCCT AACAAAACAA AAAGATGGGG TTATTCCCTA AACTTCATGG
AAATTTGGGA TTGTTTTGTT TTTCTACCCC AATAAGGGAT TTGAAGTACC 60         70         80         90        100
GCTACATAAT TGGAAGTTGG GGAACTTTGC CACAGGATCA TATTGTACAA
CGATGTATTA ACCTTCAACC CCTTGAAACG GTGTCCTAGT ATAACATGTT 110        120        130        140        150
AAGATCAAAC ACTGTTTTAG AAAACTTCCT GTTAACAGGC CTATTGATTG
TTCTAGTTTG TGACAAAATC TTTTGAAGGA CAATTGTCCG GATAACTAAC 160        170        180        190        200
GAAAGTATGT CAAAGAATTG TGGGTCTTTT GGGCTTTGCT GCTCCATTTA
CTTTCATACA GTTTCTTAAC ACCCAGAAAA CCCGAAACGA CGAGGTAAAT 210        220        230        240        250
CACAATGTGG ATATCCTGCC TTAATGCCTT TGTATGCATG TATACAAGCT
GTGTTACACC TATAGGACGG AATTACGGAA ACATACGTAC ATATGTTCGA 260        270        280        290        300
AAACAGGCTT TCACTTTCTC GCCAACTTAC AAGGCCTTTC TAAGTAAACA
TTTGTCCGAA AGTGAAAGAG CGGTTGAATG TTCCGGAAAG ATTCATTTGT 310        320        330        340        350
GTACATGAAC CTTTACCCCG TTGCTCGGCA ACGGCCTGGT CTGTGCCAAG
CATGTACTTG GAAATGGGGC AACGAGCCGT TGCCGGACCA GACACGGTTC 360        370        380        390        400
TGTTTGCTGA CGCAACCCCC ACTGGCTGGG GCTTGGCCAT AGGCCATCAG
ACAAACGACT GCGTTGGGGG TGACCGACCC CGAACCGGTA TCCGGTAGTC 410        420        430        440        450
CGCATGCGTG GAACCTTTGT GGCTCCTCTG CCGATCCATA CTGCGGAACT
GCGTACGCAC CTTGGAAACA CCGAGGAGAC GGCTAGGTAT GACGCCTTGA 460        470        480        490        500
CCTAGCCGCT TGTTTTGCTC GCAGCCGGTC TGGAGCAAAG CTCATCGGAA
GGATCGGCGA ACAAAACGAG CGTCGGCCAG ACCTCGTTTC GAGTAGCCTT 510        520        530        540 NcoI    550
CTGACAATTC TGTCGTCCTC TCGCGGAAAT ATACATCGTT TCCATGGGTC
GACTGTTAAG ACAGCAGGAG AGCGCCTTTA TATGTAGCAA AGGTACCCAG 560        570        580        590        600
TCCCCGTCTG TGCCTTCTCA TCTGCCGGTC CGTGTGCACT TCGCTTCACC
AGGGGCAGAC ACGGAAGAGT AGACGGCCAG GCACACGTGA AGCGAAGTGG
```

FIGURE 3B

```
            610         620        630        640        650
     TCTGCACGTT  GCATGGAGAC CACCGTGAAC GCCCATCAGA TCCTGCCCAA
     AGACGTGCAA  CGTACCTCTG GTGGCACTTG CGGGTAGTCT AGGACGGGTT 660         670        680        690        700
     GGTCTTACAT  AAGAGGACTC TTGGACTCCC AGCAATGTCA ACGACCGACC
     CCAGAATGTA  TTCTCCTGAG AACCTGAGGG TCGTTACAGT TGCTGGCTGG 710         720        730        740        750
     TTGAGGCCTA  CTTCAAAGAC TGTGTGTTTA AGGACTGGGA GGAGCTGGGG
     AACTCCGGAT  GAAGTTTCTG ACACACAAAT TCCTGACCCT CCTCGACCCC 760         770        780        790        800
     GAGGAGATTA  GGTTAAAGGT CTTTGTATTA GGAGGCTGTA GGCACAAATT
     CTCCTCTAAT  CCAATTTCCA GAAACATAAT CCTCCGACAT CCGTGTTTAA 810         820        830        840        850
     GGTCTGCGCA  CCAGCACCAT GCAACTTTTT CACCTCTGCC TAATCATCTC
     CCAGACGCGT  GGTCGTGGTA CGTTGAAAAA GTGGAGACGG ATTAGTAGAG 860         870        880        890        900
     TTGTACATGT  CCCACTGTTC AAGCCTCCAA GCTGTGCCTT GGGTGGCTTT
     AACATGTACA  GGGTGACAAG TTCGGAGGTT CGACACGGAA CCCACCGAAA
         NcoI
     GGGCCATGG
     CCCGGTACC
```

BICISTRONIC DNA CONSTRUCT COMPRISING X-MYC TRANSGENE FOR USE IN PRODUCTION OF TRANSGENIC ANIMAL MODEL SYSTEMS FOR HUMAN HEPATOCELLULAR CARCINOMA AND TRANSGENIC ANIMAL MODEL SYSTEMS SO PRODUCED

The present invention relates to a bicistronic DNA construct comprising X-myc transgene. In particular, the present invention relates to a bicistronic X15-myc transgene capable of expressing truncated X protein and a full-length murine c-myc protein. More particularly, the present invention relates to a bicistronic DNA construct being an X15-myc transgene for use in the production of transgenic animal model systems for human hepatocellular carcinoma and transgenic animal model systems so produced. The invention is based partially on the discovery that in susceptible transgenic mice that carry a bicistronic X-myc transgene there is an accelerated formation of liver tumors involving all lobes.

BACKGROUND OF THE INVENTION

Hepatocellular carcinoma (HCC) is one of the ten most common human cancers with over 250,000 new cases worldwide each year. Evidence gathered over decades of epidemiological studies clearly indicate that there is an indisputable association between infection due to hepatitis B virus (HBV) and HCC. The incidence of HCC is directly proportional to that of HBV. At least 50% of individuals chronically infected by HBV develop HCC. At present more than 200 million people worldwide are chronically infected. Every year one to two million die as a result of the infection, approximately 700,000 of such deaths being due to HBV associated HCC (Szmuness, 1978, Prog. Med. Virol. 24:40–69).

Although an HBV vaccine exists, the WHO estimates that 400 million people will be chronically infected by HBV by the year 2000. Since, the incubation period for the development of HBV-associated HCC is as long as 30 years or even more, the danger posed by HBV related HCC will continue to remain a major threat for decades. Therefore, there is an urgent need for better therapies to supplement existing ones such as liver resection, transplantation and ethanol injection. Otherwise, the situation is not likely to improve. However, it has been difficult to examine the pathogenic mechanism in great detail because of the limited host range of HBV and the lack of in vitro culture systems to propagate it. In view of this, most of the studies of HCC were, until recently, limited to the analysis of HBV-infected patients and chimpanzees or HBV-related hepadnavirus infections in woodchucks.

The close relationship between HBV and HCC has made it one of the most attractive and useful animal models for exploring the role of viruses in cancer development. The HBV genome has been elucidated and the viral genes implicated in hepatopathogenesis have been characterized. Insertional mutagenesis leading to the activation/ inactivation of growth regulatory genes or oncogenes as well as transactivation by viral gene products have been suggested as possible mechanisms of HBV associated carcinogenesis. The integration of HBV DNA does not show site preferences in the human genome. Nevertheless, it has been reported to integrate in the vicinity of some important cellular genes, e.g., cyclin A (Wang et al., 1990, Nature 343:555–557), retinoic acid receptors (Dejean et at., 1986, Nature 322:70–72) and oncogene hst-1 (Hatada et al., 1988, Oncogene 3:537–540). However, in case of woodchuck hepatitis virus, insertional activation of a myc gene has been observed in more than 70% of the liver tumors (Quignon et at., Oncogene 12:2011–2017).

The sequence coding for the X protein appears to play a very important role in the physiological events leading to cell transformation. A majority of patients who are seronegative for HBsAg, on evaluation by RT-PCR for transcripts of HBsAg, HBcAg and HBx, show positivity only for HBx transcripts, clearly indicating that the master molecules of HBV-mediated transformation is HBx (Paterlini et al., Hepatology 21:313–321). It also suggests that the integrated X gene may be important for maintaining the tumor phenotype. Further, HBx has been shown to transactivate a variety of viral and cellular promoters (Caselmann, 1996, Adv. Virus Res. 47:253–302) and modulate the tumor promoting pathways (Kekule et al., 1993, Nature 361:742–745; Chirillo et al., 1996, J. Virol. 70:641–646; Klein et al., 1997, Mol. Cell. Biol. 17:6427–6436). HBx binds the tumor suppressor p53 protein and disrupts the process of apoptosis (Wang et al., 1995, Cancer Res. 55:6012–6012). This action of HBx is found to interfere with the normal surveillance mechanism for removing abnormal cells. Cells with a survival advantage could be selected that in turn may trigger the multi-step process of hepatocarcinogenesis. HBx expression can transform NIH3T3 cells as well as a rodent hepatocyte cell line, FMH202 (Schaefer and Gerlich, 1995, intervirology 38:153–154). However, the cell-based transformation studies using HBx have run into trouble because these cells are quite often reported to lose their immortalized status (S. Schaefer, Personal communication). Thus, it has been extremely difficult to examine the pathogenetic mechanisms of HBV from cell culture studies and there is an urgent need for developing a proper and effective animal model system for such studies.

With the advent of embryo microinjection technology, it became evident that many questions related to HBx-associated pathogenesis might be directly examined by introduction of the X gene into transgenic mice. First, the HBx transgenic mouse line was generated in the outbred CD1 background in which the X gene was introduced under its natural promoter. High level expression of HBx induced progressive changes in the liver beginning with neoplastic lesions, through benign adenomas, and finally to malignant carcinomas that killed most male animals before 15 months of age (Kim et al., 1991, Nature 351:317–320; Koike et al., 1994, Hepatology 19:810–819). Though, these studies demonstrate the oncogenic potential of HBx, others have not observed the induction of HCC in independently developed X gene transgenic mouse strains. (Lee et al., 1990, J. Virol. 64:5939–5947; Perfumo et al., 1992, J. Virol. 66:6819–6823). This discrepancy might be associated with the promoter strength, duration of HBx expression and genetic backgrounds on which the various transgenic models were produced. This is substantiated by the fact that the mice that develop HCC were produced and maintained on CD-1 background which shows a high spontaneous rate of HCC (Homburger et al., 1975, J. Natl. Cancer. Inst. 55:37–45). This might also suggest that HBx might not be sufficient to induce HCC by itself but rather, it functions as a cofactor in the process of hepatopathogenesis. It is therefore, clear that other genetic and epigenetic events and factors are necessary for HCC to develop. In this respect, a significant acceleration of the tumorigenic process was seen in a genetic cross between the HBx transgenic and the WHV/c-myc transgenic mice (Terradillos et al., 1997, 14:395–404), but still not as fast as the pathogenetic studies demanded.

SUMMARY OF THE INVENTION

The present invention relates to a novel bicistronic DNA construct represented as X-myc transgene useful for raising animal models for HCC. In a preferred embodiment, the DNA construct is X15-myc transgene having the potential to express a truncated X protein (X15, having from 58 to 154 amino acids) that encompasses the minimal transactivation domain of HBx (Kumar et al., 1996, Proc. Natl. Acad. Sci. USA 93:5647–5652). In addition, it can express a major form of the full-length murine c-myc protein. The reasons for choosing myc gene were (a) selective amplification of c-myc gene in the HBV related HCC cases (Peng et al., 1993, J. Formos. Med. Assoc. 92:866–870) and (b) frequent activation of both c-myc gene and N-myc gene after integration of the viral DNA (Moroy et al., 1986, Nature 324:276–279; Fourel et al., 1990, Nature 347:294–298). Preferably, the X15 region is positioned 5' to the murine c-myc gene and is operatively linked to and under the regulatory control of its natural promoter and enhancer I element. The c-myc gene is operatively linked to and driven by the core promoter and enhancer II elements. The construct of the present invention is rather compact, especially in view of the fact that core promoter and enhancer II regions are embodied in the X gene sequence. No prior art known to the applicants discloses the bicistronic DNA construct i.e., X-myc transgene of the present invention. The transgenic animals of the present invention carrying such transgene develop tumors of the liver within 12–20 weeks of age, considerably faster than any transgenic animal model available. At an extremely early age itself, the transgenic animals show progressive changes in the liver as revealed by histological examinations, beginning with neoplastic lesions to benign adenomas and finally full blown malignant carcinoma within 12 to 20 weeks of age. Animals of either sex are affected and large tumors develop in all lobes of the liver. Animal models developed earlier in the out bred CD1 background exhibit a much delayed HCC resulting in the death of male mice between 11 to 15 months of age and female mice between 17 to 21 months of age (Kim et al., 1991, 351:317–320). Thus, the transgenic animal model systems for HCC of the present invention are superior to any transgenic animal model system for HCC known in the art in that the transgenic animals of the present invention develop more aggressive and accelerated onset of malignant liver tumors in all lobes causing death of the affected animals in 20 to 22 weeks, i.e., faster than the time it takes the other known transgenic animals to even develop a tumor.

Terradillo et al., (Oncogene 1997, 14:395–404) teaches the closest prior art. This prior art discloses bitransgenic mice that developed hepatocellular carcinoma in less than 60 weeks of age. Fifty percent of the animals (T50) produced liver cancer within 38 weeks. These animals were raised by crossing the following transgenic lineages:

(a) HBx transgenic mice (two lines: PEX7 and AX-16): These mice carry a transgene having two or three tandem repeat of the HBx gene under the control of either X promoter, core promoter or a erithrombin III core promoter. These animals do not develop any pathology over two years of observation.

(b) WHV/c-myc mice (two lines: 93–7 and 93–10): These mice carry a transgene having the c-myc gene (exons 1+2+3) under the control of its natural P1 promoter. The P1 promoter was placed under the control of a rearranged genomic DNA sequence of the woodchuck hepatitis virus (WHV) having the core gene, S gene, enhancer I and a 65 bp region of the X gene. These animals develop liver tumor (T50) by 48–50 weeks of age.

There could be several reasons for the delay in the onset of liver cancer in the Terradillos transgenic mice. Without wishing to be bound by theory, the applicants believe that it is the lack of proximity of the X gene or the flanking regulatory sequences to the c-myc gene that causes delay in the onset of liver cancer. In spite of recognizing this fact, it has hitherto not been possible to produce a bitransgenic mice having the X gene or the flanking regulatory sequence fused with or even sufficiently close to the c-myc gene for the former to influence the latter sufficiently early to bring about an accelerated onset of liver cancer. Neither has it been possible to have the two transgenes integrated on the same chromosome, close enough to each other, to allow manifestation of accelerated onset of liver cancer. In fact, it is practically impossible for a genetic recombination to achieve such proximity, leave alone an integrated construct for the reason that in the WHV/c-myc transgene the X open reading frame and the core promoter/enhancer II elements are missing. In addition, the C-myc gene has three exons, all of which are driven by its own P1 promoter. Secondly, in the HBx transgenic mice the X gene has been placed under three independent promoters thereby, further reducing the probability of recombination. Thirdly, the respective transgenes are invariably located on different chromosomes in the two parental or founder transgenic mice. Consequently, the two transgenes are never integrated in the same chromosome in the descendants, as a result of which these transgenic mice always develop a highly delayed onset of hepatocellular carcinoma. Even hypothetically assuming that two founder mice carry their respective transgenes on identical chromosomes, the descendants will still have the trangenes located on different loci, even on the same chromosome. Such lack proximity again causes delay in the onset of liver cancer. As far as the applicants are aware, there is no evidence that the two transgenes have ever been integrated in the same chromosome of any transgenic mice. It was realized by the applicants, for the first time, that the proximity of X gene to c-myc gene played a crucial role in the accelerated onset of hepatocellular carcinoma and that the only way the closest proximity could be achieved was by bringing together the X gene, preferably, the truncated X15 version and the murine c-myc gene outside the mice as a bicistronic X15-c myc construct transgene and thereafter, introducing such transgene into the mice or ancestors thereof at an embryonic stage.

DETAILED DESCRIPTION OF THE INVENTION

"The file of this patent contains at least one drawing or photograph executed in color. Copies of this patent with color drawing(s) or photograph(s) will be provided by the Patent and Trademark Office upon request and payment of necessary fee."

The invention will now be described in greater detail with reference to the accompanying drawings in which:

FIG. 1 discloses a diagrammatic representation of the regulatory elements in the HBV genome (adw sub type).

FIG. 3 depicts the sequence of the regulatory and coding regions of the X15 component in the X-myc construct. (SEQ ID NO: 1).

X15-MYC FUSED TRANSGENES

Gene fusions were made using truncated X gene (X15, amino acids 58 to 154) and murine c-myc gene. The myc gene is known to be an activatable oncogene. The regulatory and coding regions of the X gene are shown in FIG. 3 and constitute a crucial part of the construct of the present invention. The complete nucleotide sequence of the murine c-myc gene (MUSCMYC1, Exons 1, 2 and 3) will be well known to a person skilled in the art and is available under European Microbiological Lab (EMBL) Accession numbers L00038, J00373 and J00374.

Figure 1:
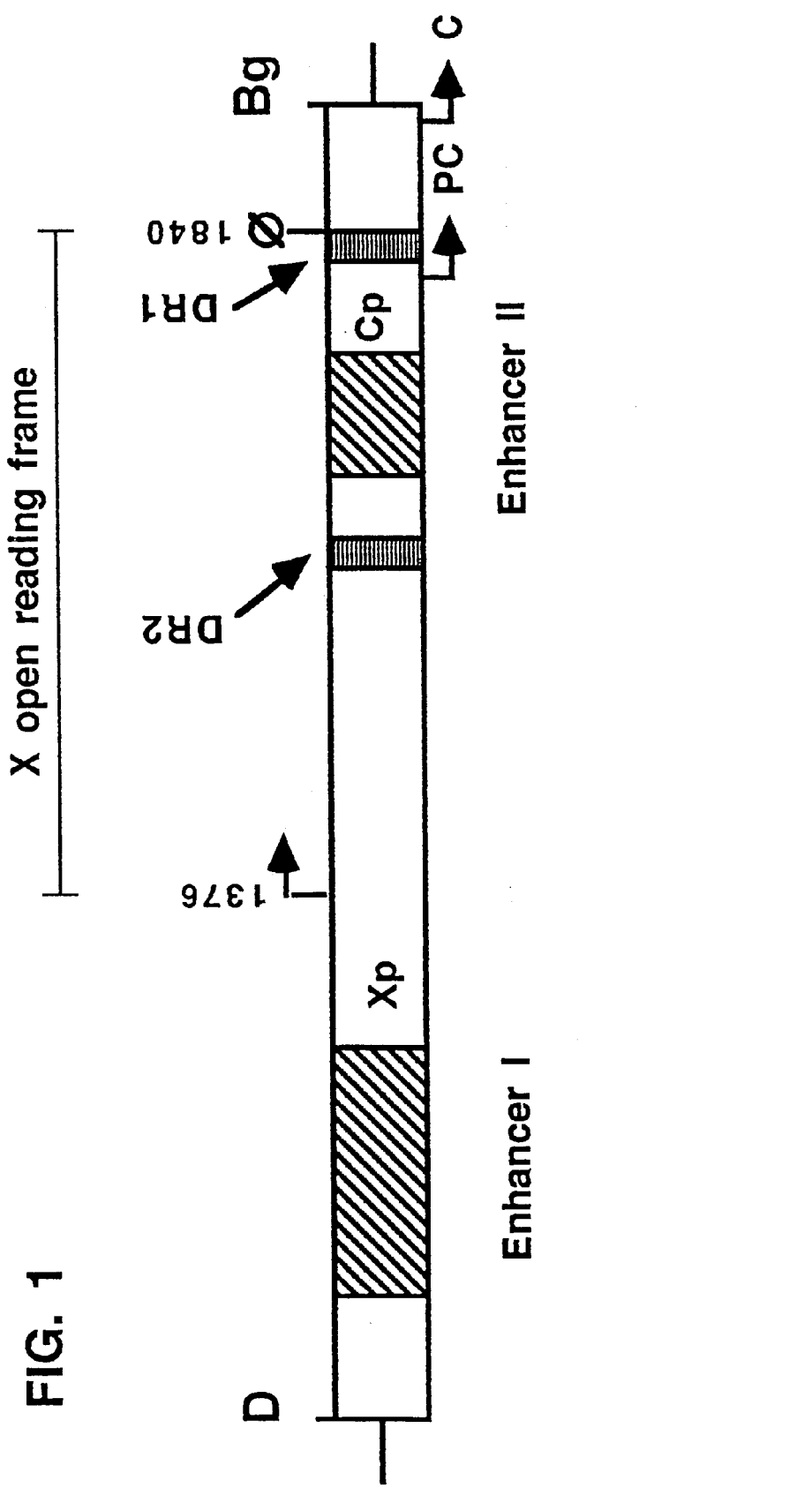

The regulatory elements, in the HBV genome are diagrammatically illustrated in FIG. 1. Restriction sites are shown in the Figure in which D is DraI site, Bg is Bgl II site. Xp is the natural X promoter which controls the X protein in the construct (FIG. 2) of the invention while Cp is the core promoter which drives the myc gene of the construct. DR1 and DR2 represent the direct repeats 1 and 2 respectively in the X open reading frame.

Figure 2:
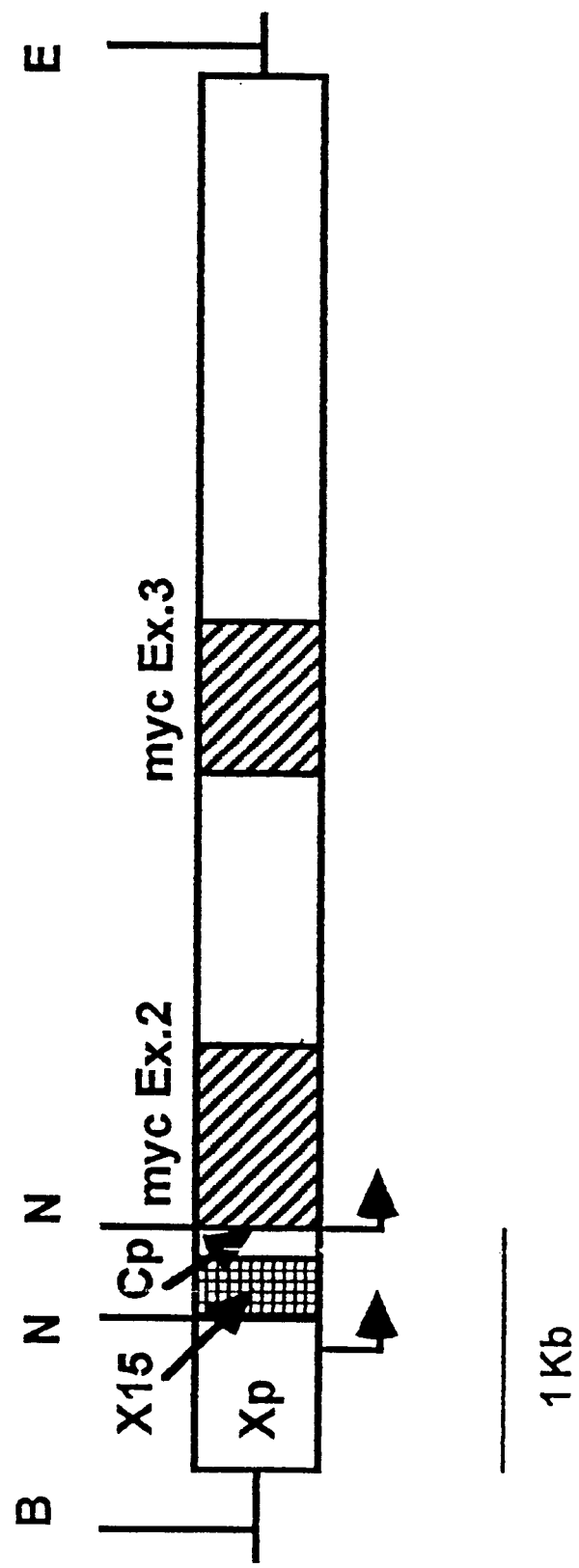
FIG. 2 shows a diagrammatic representation of the X15-myc bicistronic construct.
Figure 4A:
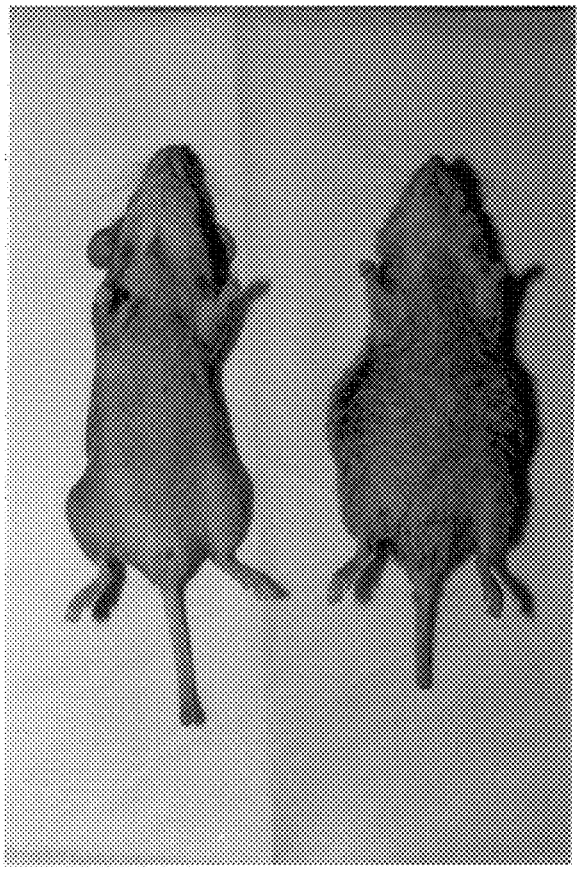
FIG. 4(A) is a photograph of the pectoral view of 14-week-old mouse littermates. The mouse on the right is the transgenic X15-myc mouse.
Figure 4B:
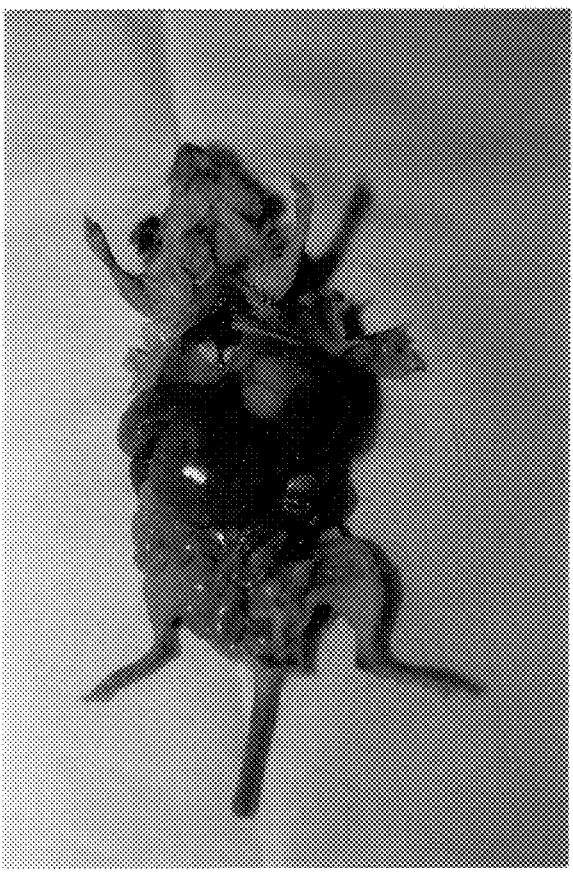
FIG. 4(B) is photograph of viscera of the transgenic animal after dissecting it from the ventral side.
Figure 4C:
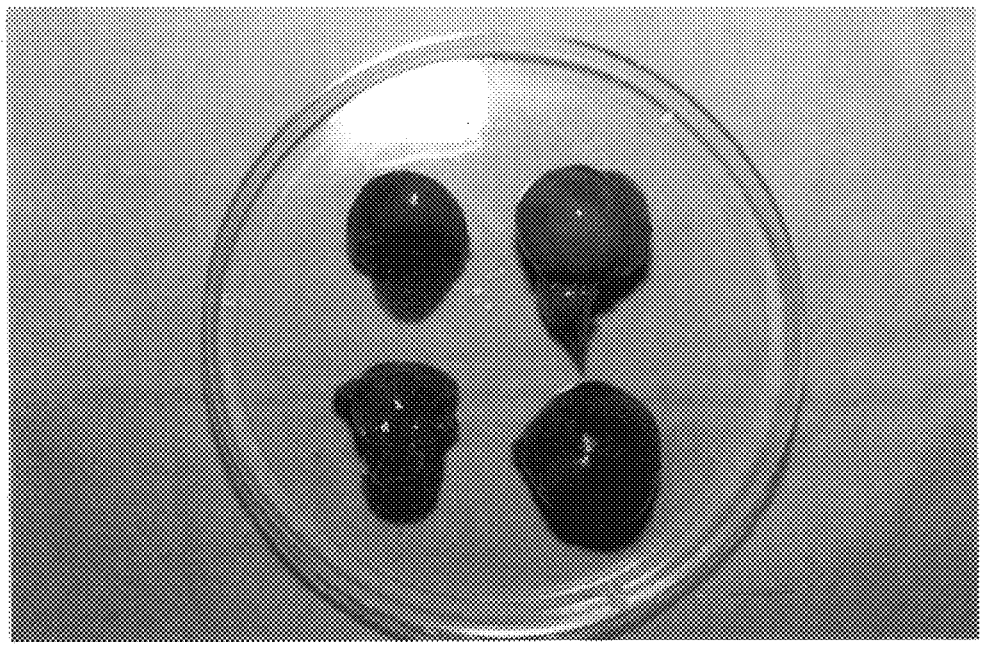
FIG. 4(C) is the photograph taken of four lobes of the liver of the transgenic mouse of FIG. 4(B) after they were separated and transferred to a petri dish.
Figure 4D:
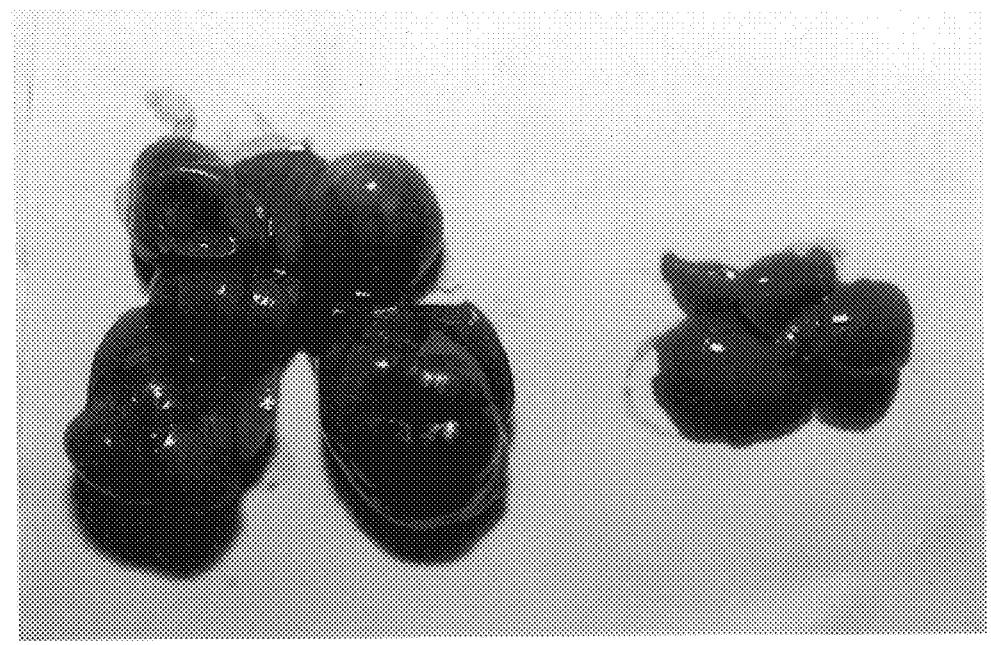
FIG. 4(D) shows liver tissues from a normal and a transgenic animal.
Figure 5A:
FIG. 5 shows microphotographs of liver sections of a 14-week-old X15-myc transgenic animal.
Figure 5B:
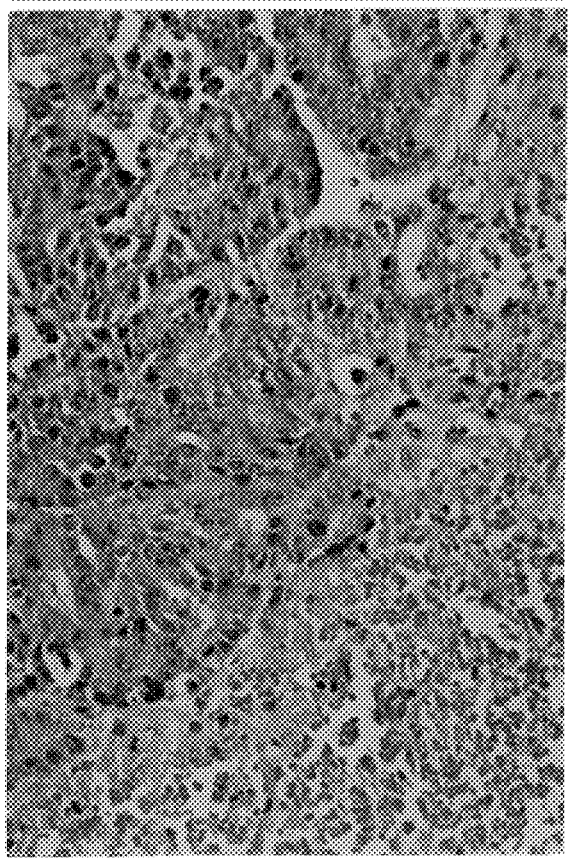
Figure 5C:
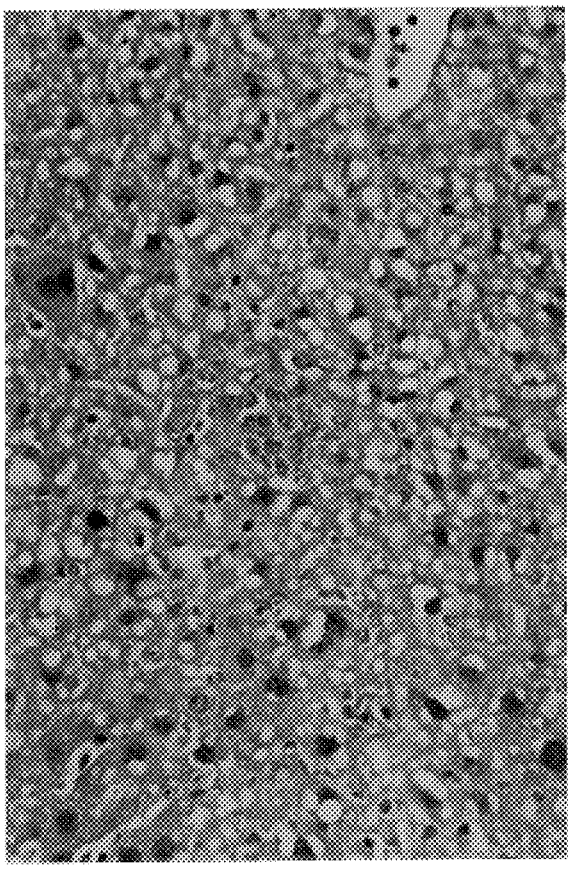
Figure 5D:
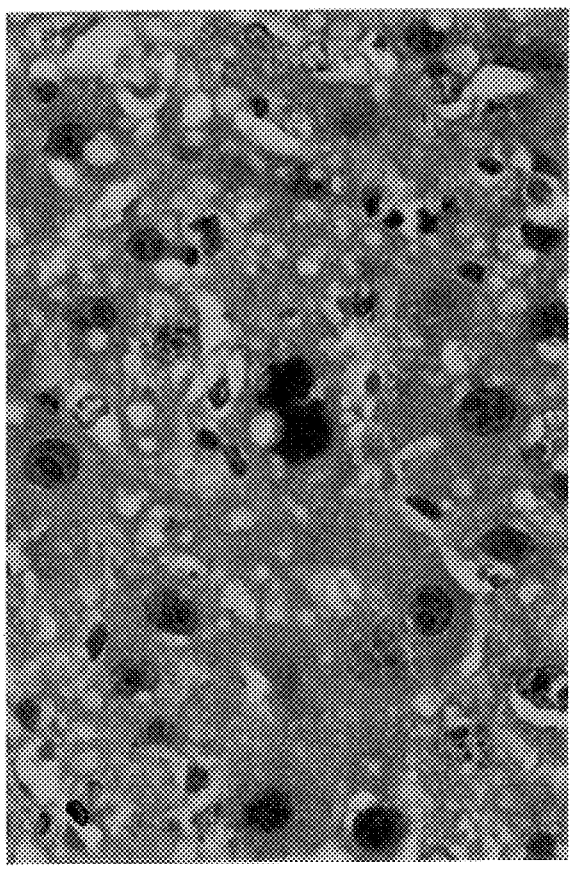

The bicistronic X15-myc transgene DNA construct is diagrammatically shown in FIG. 2. The mutant X15 gene is operatively linked to and under the control of the natural X promoter Xp including enhancer I. In this recombinant, the murine c-myc gene (Exons 2 and 3) is driven by the core promoter Cp and enhancer II elements. B represents Bam HI site, N represents Nco I sites and E represents Eco RI site. The recombinant is constructed as follows:

(a) the murine c-myc gene is subjected to a site directed mutagenesis to create an Nco I site near the first methionine codon of exon 2 thereof to produce a c-myc (2+3) gene. A person skilled in the art will know how to carry out a site directed mutagenesis step.

(b) a 539 bp DraI-Nco I fragment of the HBV genome (adw sub type) encompassing the enhancer I and X promoter regions was joined by conventional methods with the c-myc (2+3) gene to generate Xp-myc gene.

(c) a 362 bp fragment of the HBV genome encompassing the coding region for the C-terminal half of the X gene having from 58 to 154 amino acids along with enhancer II and core promoter regions was PCR amplified. This was then cloned as Nco I fragment in the Xp-myc construct to generate X15-myc construct. The following two primers were employed in the polymeric chain (PCR) reaction:

HBx11:
5'-CGGAATTCCATGGGTCTCCCCGTCTGTGC-3' (SEQ ID NO: 2)

HBx19: 5'-CGGAATTCCATGGCCCAAAGC-3'. (SEQ ID NO: 3)

As will be known to persons skilled in the art, the orientation of the X15 fragment can be verified by sequencing.

PRODUCTION OF TRANSGENIC NON HUMAN MAMMALS CONTAINING BICISTRONIC X-MYC TRANSGENE

The invention concerns a non-human mammal, preferably a rodent, more preferably a mouse. It is, important that the development of hepatocellular carcinoma in the animal model closely parallels the development thereof in humans. Like human beings, staged development of neoplastic lesions, through benign adenomas, and finally malignant carcinomas involving all lobes of the liver occurs in the mouse of the invention. Therefore, mouse is preferred as the ideal model for the purposes of the invention.

Another advantage of using the mouse is the pace at which the cancer of the liver develops enabling the evaluation of drugs and other therapeutic agents or screening of suspect compounds to be carried out in less than 12 to 20 weeks.

It will however, be readily understandable to a person skilled in the art that the invention is not limited to a mouse but other non human mammals such as rats, rabbits, guinea pigs, pigs or non human primates may be successfully employed. There are several known methods for producing and raising transgenic animals. The most common method involves directly injecting the transgene into the embryo. The present invention successfully utilizes this method. The present invention also encompasses use of other known methods including but not limited to transfecting retrovirus method, electroporation, cell gun, cell fusion or embryonic stem cell methodology. In a preferred embodiment, the present invention utilizes microinjection method described in Wagner et al., 1981, Proc. Natl. Acad. Sci, USA 78:5016–5020. Briefly, this method involves microinjecting a recombinant nucleic acid construct into the fertilized eggs. By way of example, fertilized eggs may be collected from recently mated females with vaginal plugs. After microinjection, the eggs may be transferred to pseudopregnant females, which had been mated the night before to vasectomized males. It is preferred that the fertilized eggs are at a single celled oocyte stage and preferably not more than 8-cell stage. Introduction of transgene constructs into a single celled fertilized oocyte will ensure that it will be present in all the germ cells and somatic cells of the transgenic founder animal. This in turn will ensure that all the descendants of the founder animal will carry the transgene in all their germ cells and somatic cells. Introduction of the transgene at an advanced embryonic stage may produce a transgenic founder animal, some of the somatic cells of which may lack the transgene sequence. However, the descendants of such animals, which inherit the transgene, will carry it in all their germ cells and somatic cells. Later embryonic stage is preferably avoided because it is cumbersome to micro inject all the nuclei although, it is possible to do so.

It is preferable to produce a genetically homologous line of animals. It is recommended that animals, which are themselves, members of an inbred, fully characterized strain are employed. The advantage of using a genetically homologous line is that these animals will produce functionally reproducible tumor model systems. In a genetically heterogeneous line, inconsistent tumor model systems may be displayed owing to interaction of the transgene with other gene products, which may vary from animal to animal due to gene segregation in the progeny.

The present invention advantageously employs the following illustrative and non-limitative embodiment:

An X15-myc fragment (5.7 Kb EcoRI-BamHI fragment) prepared in accordance with the present invention was cloned in a plasmid vector. It was the cut and digested by employing readily available conventional enzymes. The preferred enzymes employed were selected from the group consisting of Eco R I and Bam H I. The cut product was purified by sucrose density centrifugation (5–20%). The DNA concentration was adjusted to 4 ng/µl in Tris (10 mM)—EDTA (0.1) buffer and microinjected into male pronucleus of fertilized eggs. The eggs were preferably derived from second generation progeny of SJL×C57/B6 mating. The micro injected eggs were then transferred to pseudo pregnant foster females as described in Wagner et at., 1981, Proc. Natl. Acad. Sci, USA 78:5016–5020, referred to above and preferably, housed in an environmentally controlled facility. Preferably, such facility is maintained on a 10-hour dark, 14-hour light cycle. The eggs in the foster female were allowed to develop to term and the pups delivered in the usual manner.

ANALYSIS OF TRANSGENIC MICE

The founder animals were analyzed using genomic DNA isolated from the tails in Southern hybridization method by employing a nick translated probe (32P DNA probe) corresponding to the X15 component of the construct. The extraction of DNA from the tails and the exact method of analysis are well known to persons skilled in the art. The Southern hybridization method indicated that 2% of founder animals carried X15-myc gene. The positive founder animals were bred further and at four weeks of age the pups were again subjected to Southern hybridization described above. The applicants have so far produced five generations of mice and have collected over 200 mice having the X15-myc transgene. The applicants have optimized the PCR strategy (410 bp amplifications) for analyzing the animals of new generation as follows:

Xp-F: 5'-TGG GCT ACA TAA TTG GAA GTT G-3' (SEQ ID NO: 4)

Xp-R: 5'-GGC TAG GAG TTC CGC AGT ATG-3' (SEQ ID NO: 5)

The transcripts for the X15 and myc genes were analyzed using well known S1-mapping and northern hybridization techniques.

ASSAYS EMPLOYING TRANSGENIC ANIMALS OF THE INVENTION FOR CARCINOGENICITY TESTING

The transgenic animals of the present invention are advantageously employed for screening materials suspected of being a carcinogen. If the material in question is suspected of being only a weak carcinogen, transgenic mice, which are most susceptible to developing cancer, are employed. Such animals are selected by exposing a group of transgenic mice to a known carcinogen and selecting those, which develop tumors fastest. The selected animals and their descendants are then employed as test animals and exposed to the material in question suspected of being a carcinogen. The extent of neoplastic growth in these animals will be an indicator of carcinogenicity. Other susceptible animals from the same group may be used as control animals, which are not exposed to the material in question. The difference in rate of development of neoplastic lesions will again act as an indicator of the carcinogenicity of the material in question. Likewise, less sensitive animals can be used for testing strongly carcinogenic materials. A person skilled in the art will know how to select animals of desired sensitivity by varying the type and concentration of the known carcinogens used in the selection process.

IN VIVO SCREENING ASSAY FOR DETERMINING EFFICACY OF THERAPEUTIC AGENTS

The transgenic animals of the present invention are most useful animal models for hepatocellular carcinoma and agents and procedures useful for the diagnosis and treatment thereof. Treatments that potentially cure HCC may be first tested on the transgenic mice that have developed tumors at different stages and comparing the effects of treatment with untreated controls at similar stages of the decease.

HISTOLOGICAL AND PATHOGENETIC STUDIES

The transgenic animals of the present invention can be employed as a source of cells for cell and tissue culture. Following conventional methods, the tissues of the transgenic animals may be analyzed for the presence of the activated transgene either by DNA or RNA analysis or by assaying the tissue for the protein expressed by the gene. Cells of tissues carrying the gene can be cultured by methods known in the art and used to study the causes that lead to HCC and especially, the influence of the X protein on myc gene and other pathological factors that lead to the accelerated onset of HCC.

It will be readily apparent to a person skilled in the art that the invention is not limited to the preferred embodiments described herein. Other variations and modifications of the invention are possible without departing from the spirit or scope of the invention which is limited only by the claims appended hereto.

---

What is claimed is:

1. A bicistronic hepatitis B virus (HBV) X15-c-myc transgene, wherein said HBV X15-c-myc transgene comprises in sequence: a HBV X15 transgene and a c-myc transgene;

wherein said bicistronic HBV X15-c-myc transgene encodes a truncated HBV X15 protein comprising amino acids 58–154 of HBV X15 and a murine c-myc protein, wherein said HBV X15 transgene comprises the nucleotide sequences disclosed in SEQ ID NO:1 and said murine c-myc transgene comprises exons 2 and 3 of murine c-myc;

wherein said HBV X15 transgene is operatively linked to and under the regulatory control of its natural HBV X15 promoter and enhancer I elements and the c-myc transgene is operatively linked to and under the regulatory control of a core promoter and an enhancer II element of the HBV X15 gene.

2. A transgenic mouse wherein the germ cells and somatic cells of the transgenic mouse comprise a bicistronic HBV X15-c-myc transgene, wherein said HBV X15-c-myc transgene comprises in sequence: a HBV X15 transgene and a c-myc transgene;

wherein said bicistronic HBV X15-c-myc transgene encodes a truncated HBV X15 protein comprising amino acids 58–154 of HBV X15 and a murine c-myc protein, wherein said HBV X15 transgene comprises the nucleotide sequences disclosed in SEQ ID NO:1 and said murine c-myc transgene comprises exons 2 and 3 of murine c-myc;

wherein said HBV X15 transgene is operatively linked to and under the regulatory control of its natural HBV X15 promoter and enhancer I elements and the c-myc transgene is operatively linked to and under the regulatory control of a core promoter and an enhancer II element of the HBV X15 gene; and wherein the expression of said HBV X15-c-myc transgene results in development of hepatocellular carcinoma in the transgenic mouse.

3. A method of screening a candidate substance to determine whether said candidate substance promotes hepatocellular carcinoma, wherein said method comprises the steps of:

(i) providing a transgenic mouse wherein the germ cells and somatic cells of the transgenic mouse comprise a bicistronic HBV X15-c-myc transgene, wherein said HBV X15-c-myc transgene comprises in sequence: a HBV X15 transgene and a c-myc transgene;

wherein said bicistronic HBV X15-c-myc transgene encodes a truncated HBV X15 protein comprising amino acids 58–154 of HBV X15 and a murine c-myc protein, wherein said HBV X15 transgene comprises the nucleotide sequences disclosed in SEQ ID NO:1 and said murine c-myc transgene comprises exons 2 and 3 of murine c-myc;

wherein said HBV X15 transgene is operatively linked to and under the regulatory control of its natural HBV X15 promoter and enhancer I elements and the c-myc transgene is operatively linked to and under the regulatory control of a core promoter and an enhancer II element of the HBV X15 gene; and wherein the expression of said HBV X15 transgene results in the development of hepatocellular carcinoma in the transgenic mouse;

(ii) exposing said transgenic mouse to said candidate substance; and (iii) monitoring said transgenic mouse for the development of hepatocellular carcinoma;

(iv) wherein an increase in the development of hepatocellular carcinoma in the transgenic mouse exposed to said candidate substance compared to the development of the hepatocellular carcinoma in a transgenic mouse not exposed to said candidate substance indicates that the candidate substance promotes hepatocellular carcinoma.

4. A method of making a bicistronic HBV X15-c-myc transgene DNA construct comprising (a) subjecting a murine c-myc gene to a site directed mutagenesis to create an Nco I site near the first methionine codon of exon 2 thereof to produce a c-myc (2+3) gene comprising nucleotide sequences encoding exons 2 and 3 of c-myc;

(b) joining a 539 base pair Dra I-Nco I fragment of the HBV genome encompassing the enhancer I and X promoter regions said c-myc (2+3) gene to generate Xp-c-myc gene; and (c) amplifying by polymerase chain reaction (PCR) a 362 base pair fragment of the HBV genome encompassing a coding region for the C-terminal half of the X gene, wherein the coding region encodes amino acids 58–154 of HBVX15, an enhancer II and a core promoter region, and cloning the 263 base pair fragment into the Nco I site of the Xp-c-myc construct to generate the HBV X15-c-myc transgene.

5. A method as claimed in claim 4 wherein primers employed in the PCR consist of the sequences disclosed in SEQ ID NO: 2 and SEQ ID NO: 3.

* * * * *

SEQUENCE LISTING

<160> NUMBER OF SEQ ID NOS: 5

<210> SEQ ID NO 1
<211> LENGTH: 909
<212> TYPE: DNA
<213> ORGANISM: Hepatitis B virus

<400> SEQUENCE: 1

```
tttaaaccct aacaaaacaa aaagatgggg ttattcccta aacttcatgg gctacataat      60
tggaagttgg ggaactttgc cacaggatca tattgtacaa aagatcaaac actgttttag     120
aaaacttcct gttaacaggc ctattgattg gaaagtatgt caaagaattg tgggtctttt     180
gggctttgct gctccattta cacaatgtgg atatcctgcc ttaatgcctt tgtatgcatg     240
```

```
tatacaagct aaacaggctt tcactttctc gccaacttac aaggcctttc taagtaaaca     300
gtacatgaac ctttaccccg ttgctcggca acggcctggt ctgtgccaag tgtttgctga     360
cgcaaccccc actggctggg gcttggccat aggccatcag cgcatgcgtg aacctttgt     420 ggctcctctg ccgatccata ctgcggaact cctagccgct tgttttgctc gcagccggtc     480
tggagcaaag ctcatcggaa ctgacaattc tgtcgtcctc tcgcggaaat atacatcgtt     540
tccatgggtc tccccgtctg tgccttctca tctgccggtc cgtgtgcact tcgcttcacc     600
tctgcacgtt gcatggagac caccgtgaac gcccatcaga tcctgcccaa ggtcttacat     660
aagaggactc ttggactccc agcaatgtca acgaccgacc ttgaggccta cttcaaagac     720
tgtgtgttta aggactggga ggagctgggg gaggagatta ggttaaaggt ctttgtatta     780
ggaggctgta ggcacaaatt ggtctgcgca ccagcaccat gcaacttttt cacctctgcc     840
taatcatctc ttgtacatgt cccactgttc aagcctccaa gctgtgcctt gggtggcttt     900
gggccatgg                                                             909

<210> SEQ ID NO 2
<211> LENGTH: 29
<212> TYPE: DNA
<213> ORGANISM: Hepatitis B virus

<400> SEQUENCE: 2
cggaattcca tgggtctccc cgtctgtgc                                        29

<210> SEQ ID NO 3
<211> LENGTH: 21
<212> TYPE: DNA
<213> ORGANISM: Hepatitis B virus

<400> SEQUENCE: 3
cggaattcca tggcccaaag c                                                21

<210> SEQ ID NO 4
<211> LENGTH: 22
<212> TYPE: DNA
<213> ORGANISM: Hepatitis B virus

<400> SEQUENCE: 4
tgggctacat aattggaagt tg                                               22

<210> SEQ ID NO 5
<211> LENGTH: 21
<212> TYPE: DNA
<213> ORGANISM: Hepatitis B virus

<400> SEQUENCE: 5
ggctaggagt tccgcagtat g                                                21
```